United States Patent [19]
Clark

[11] 4,269,065
[45] May 26, 1981

[54] ULTRASONIC DETECTOR APPARATUS

[76] Inventor: Robert N. Clark, 530 E. Lime, Lakeland, Fla. 33800

[21] Appl. No.: 67,149

[22] Filed: Aug. 16, 1979

Related U.S. Application Data

[63] Continuation-in-part of Ser. No. 882,361, Mar. 1, 1978, abandoned, which is a continuation-in-part of Ser. No. 798,821, May 20, 1977, abandoned, which is a continuation-in-part of Ser. No. 698,011, Jun. 21, 1976, abandoned.

[51] Int. Cl.³ .............................................. G01H 1/00
[52] U.S. Cl. .......................................... 73/587; 73/660
[58] Field of Search .................. 73/593, 659, 660, 587

[56] References Cited
U.S. PATENT DOCUMENTS

| | | | |
|---|---|---|---|
| 2,915,897 | 12/1959 | Hoffmann | 73/659 |
| 3,315,522 | 4/1967 | Frarey et al. | 73/659 |
| 3,400,578 | 9/1968 | Frarey et al. | 73/593 X |
| 3,416,630 | 12/1968 | Pohl et al. | 73/593 X |

*Primary Examiner*—Charles A. Ruehl
*Attorney, Agent, or Firm*—Duckworth, Hobby, Allen, Dyer & Pettis

[57] ABSTRACT

A non-destructive test apparatus for obtaining advance warning of impending mechanical failure by the detection and analysis of ultrasonic frequency signals which are generated internally by the equipment being tested. The detector apparatus of the present invention receives and displays in audible and/or visual form a primary carrier frequency which indicates wearing surfaces and which is characteristic of an incipient mechanical malfunction. The detector apparatus is further capable of recording signals received for subsequent evaluation and use by maintenance personnel as part of an integrated planned maintenance program.

8 Claims, 2 Drawing Figures

ULTRASONIC DETECTOR APPARATUS

This application is a continuation-in-part of my copending U.S. Pat. application Ser. No. 882,361, filed Mar. 1, 1978, now abandoned, which was a continuation-in-part of my prior U.S. Pat. Application Ser. No. 798,821, filed May 20, 1977, now abandoned, which was a continuation-in-part of my prior U.S. Pat. Application Ser. No. 698,011, filed June 21, 1976, now abandoned.

BACKGROUND OF THE INVENTION

1. Field of the Invention

The present invention relates to an ultrasonic detector apparatus useful for non-destructive testing of mechanical equipment whereby ultrasonic frequency signals generated internally by the equipment may be detected and analyzed to identify impending mechanical failures.

2. Description of the Prior Art

Contemporary practice for maintenance and repair is primarily dependent upon the detection of audible sounds emitted from the equipment. Such audible sounds indicate a failure mode of operation, and do not generally occur substantially prior to failure to affect their timely repair. Current maintenance procedures generally include elaborate instrumentation, sensor installation, involved data collection and mathmodel analysis as well as the use of an expensive and highly trained engineering staff. Accordingly state-of-the art malfunction detectors normally involve physical attachment of at least a portion of the device to the mechanical equipment, and often utilize a signal reflected from the detector, rather than a signal generated by the equipment, as the means for analyzing and determining equipment malfunction.

U.S. Pat. No. 3,858,439 to Nakamura teaches such a method and apparatus wherein master sensors are actually placed on the structure to be tested. U.S. Pat. No. 3,986,391 to Vahaviolos teaches an apparatus for monitoring a continuous weld by detecting and processing stress wave signals emitted from the weld area as the material is heated and subsequently cooled. A similar teaching calling for physical contact of the sensor to the source of acoustic emissions is taught in U.S. Pat. No. 4,033,179. Finally U.S. Pat. No. 3,681,978 to Mathias shows a method and apparatus for automatically balancing a periodic deflection signal being produced by deflection sensors which are actually applied to a rotating body.

In contrast to these prior art devices, the present invention is non-destructive, passive in that the detector apparatus does not generate ultrasonic frequencies but merely receives, interrogates and stores them, and does not require attachment to or physical contact with the equipment being tested, thereby allowing substantial portability and ease of use. In principle the present invention teaches that the wearing of components within a piece of equipment emits signals in the ultrasonic frequency range which can be detected by a hand-held sensor while the equipment is still operating, also that these signals can be analyzed to detect an incipient malfunction, both normal and abnormal wear of the equipment, and, further, that such signals can be used to project time-to-failure of the equipment component. In view of the above, it is one object of the present invention to provide a means to detect an incipient malfunction which avoid the problems associated with the prior art and as yet unresolved.

Another object of this invention is to enable the detection of normal and abnormal wear without physical contact of the equipment while the equipment is still in its normal operation mode, and to enable analysis of the signals from the equipment with a minimum of technical expertise by use of a segmented display which indicates the result of a single test and by the use of plural displays to indicate the results of successive test series in order to discriminate between normal and abnormal wear. Yet another object of the present invention is to provide a decrease in ambient background noise to improve signal quality. Finally, it is further intended that use of the ultrasonic detector apparatus of this invention will enable the user to project a time-to-failure of the operational equipment, thereby establishing priorities of maintenance and economical equipment usage prior to its repair. Further objects of the invention will in part be obvious and will in part appear hereinafter.

SUMMARY OF THE INVENTION

The present invention for an ultrasonic detector apparatus teaches a device for the detection and analysis of equipment generated ultrasonic signals due to the operational processes and continuous wearing of components and moving parts. These signals are propagated into the surrounding space. According to one mode of operation taught by the invention, detection of this primary carrier frequency is indicative of an incipient malfunction. A second mode of operation teaches that this carrier frequency is modulated with many signals which vary in phase, frequency and amplitude, producing a characteristic rhythm when the equipment ages normally, while spasmodic and adbrupt signals are indicative of abnormal wear and potential malfunction. Another aspect of the invention teaches that the primary carrier frequency decreases at a predictable rate consistent with component wear, and that a potential failure of that part or component can be projected, within relative limits, at some discrete future time by observation and calculation of the rate at which the primary frequency decreases from one center frequency to another and that extrapolation of this rate of change as to when the carrier frequency will enter the failure mode. Failure is not a primary readable signal; however, it is within the concept of this invention that the apparatus may forewarn failure by proper evaluation of signals generated.

The invention accordingly comprises the features of construction, combination of elements, and arrangement of parts which will be exemplified in the construction hereinafter set forth, and the scope of the invention will be indicated in the claims. Circuit components are not germain to the disclosure herein and are not detailed in the attempt to promote better understanding, clairity and definition of this complex and highly technical subject matter.

BRIEF DESCRIPTION OF THE DRAWINGS

For a fuller understanding of the nature and objects of the invention, reference should be had to the following detailed description taken in connection with the accompanying drawings, in which.

DETAILED DESCRIPTION

The ultrasonic detector apparatus of this invention can be employed in various modes of operation, as will be taught hereinafter, to provide a non-destructive tool applicable to equipment of various types, uses, complexities. For purposes of illustration only the apparatus will be described in its application to dynamic operational equipment components which generate internal signals due to wear, friction and operation and the like. The observation frequency range for the present invention has been determined to be most effective between 30,000 hertz and 120,000 hertz, but is not limited to this range. The detector apparatus used herein comprises a free space resonant piezoceramic element with a center frequency of 40 khz, and this too, is intended for purposes of illustration and not limitation.

Figure 1:
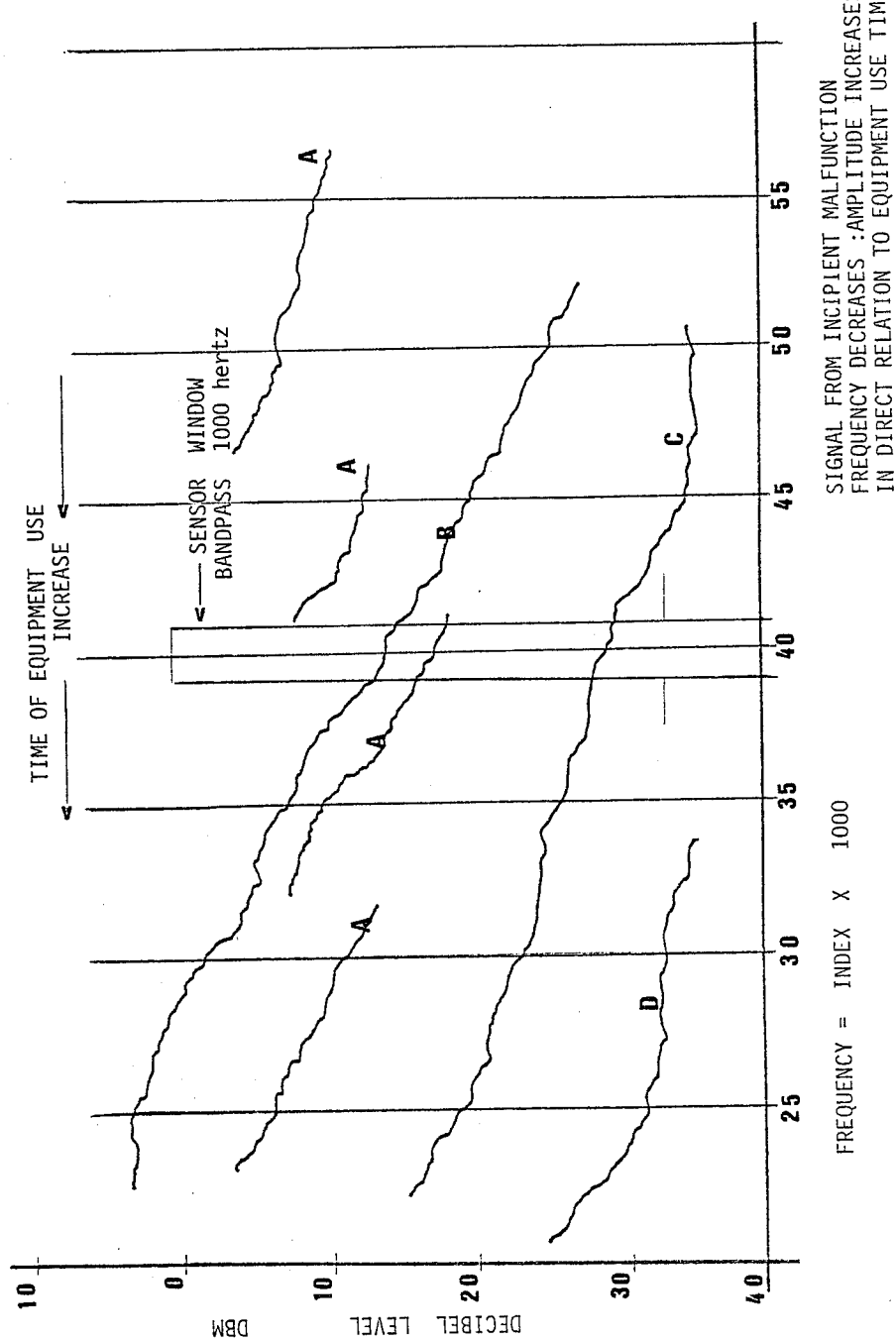
FIG. 1 is a graphic representation of characteristic signals emitted from operating machinery illustrating that such emissions decrease in frequency and increase in signal intensity as the incipient malfunction ages. The shaded area represents the bandpass of a selected sensor.

Referring to the graphic representation of FIG. 1 there is depicted therein a history of change in the primary carrier frequency and energy level due to characteristics of an incipient malfunction of equipment components. It should be noted that the view of FIG. 1 depicts the results of tests conducted at four discrete locations as identified by the reference letters A,B,C and D. Remembering that a detection device with a center frequency of 40 khz was utilized, no signal was present for evaluation until it entered the "window" of the sensor element. Yet, in fact, such signal had existed prior to entering the window, and did continue to exist at lower frequencies. Appearance of the ultrasonic signal within the window becomes indicative of an incipient malfunction, and it can be seen that once the progression has started toward the lower frequencies that trend is relatively unchanged. Where there are abrupt changes of signal level, this was due to lubrication or adjustment of the equipment and it can be seen that the frequency remained relatively unchanged.

It becomes imperative to detect the incipient malfunction and monitor its activity. Noting the time required for the primary carrier frequency to pass through the sensor window will enable calculation of the time required for the carrier frequency to decrease 1 khz, which is the width of the window of the sensor. As can be seen in FIG. 1, this rate of change is relatively linear. Therefore a projection can be made as to when failure can be expected. For example, should it take three days for the carrier frequency to traverse the 1 khz sensor bandpass, and if a failure margin of safety is established at 25 khz, then about forty-five days will elapse before the "failure mode" is reached.

It is also desirable to catalog the various locations where indications were detected to insure that these locations are monitored and analyzed on a scheduled basis, and that maintenance reports reflect any peculiar activity at these points such as heated surfaces, lubrication, speed adjustment, belt replacement and so forth.

Further examination of the primary carrier frequency, using a spectrum analyzer, will indicate that this center frequency is modulated with random signals which vary in composition of phase, frequency and amplitude, producing a chracteristic rhythm when the equipment is wearing normally, whereas spasmodic and abrupt signals of modulation will indicate abnormal or faulty wear further indicating a potential malfunction.

The ultrasonic detector apparatus may further comprise phase lock loop circuits, each tuned to a specific frequency so as to indicate on a segmented display which frequencies are present during a given test. Several segmented displays will indicate the immediate results of several test cycles for comparison purposes. When each of the plural displays indicate in substantially identical fashion, the modulated signal is relatively continuous or rhythmical and wear is normal. However, when the segments of the plural display indicate in a random manner, this is indicative of abnormal wear and preventive maintenance must be performed within a relatively short period of time.

Exhaustive testing has been performed to determine generally at which point specific equipment will fail (including a safety factor), to determine time-to-failure of a particular component so as to establish a finite time when the equipment should be repaired upon determination of an incipient malfunction. For purposes of economy, and safety, maintenance should be performed immediately prior to the established failure mode. Computation of this time-to-failure is based upon the relatively linear rate at which the frequency decreases, and is calculated as set forth above.

Equipment components may generate mechanical energy release (ultrasonic signals) over a life cycle of many months duration having a tendency, in time, to increase in amplitude and decrease in frequency as mechanical wear becomes more critical. The life cycle may not enable continuous mapping as shown in FIG. 1; however, the emitted energy will generally traverse the spectrum as indicated. In the system embodiment of the present invention, signals are monitored close to the source of emanations and amplified to the degree necessary for processing the signal electronically to investigate specific characteristics. The component or machine under investigation must emit a predominant carrier frequency propagated within the response range (window) of the selected sensor. Data evaluation by proper criteria can only suggest a potential malfunction; thus physical inspection will be required to establish actual repair priorities. The apparatus of this invention will further permit data collection for component history records and equipment analysis. Proper interpretation of the signal data will enable selective maintenance, priority repair, or timely component replacement. Each characteristic can be individually cataloged and recorded for a particular piece of equipment or component which can bebe compared and evaluated during successive testing schedules to determine the severity of the signal change and other pertinent information.

Figure 2:
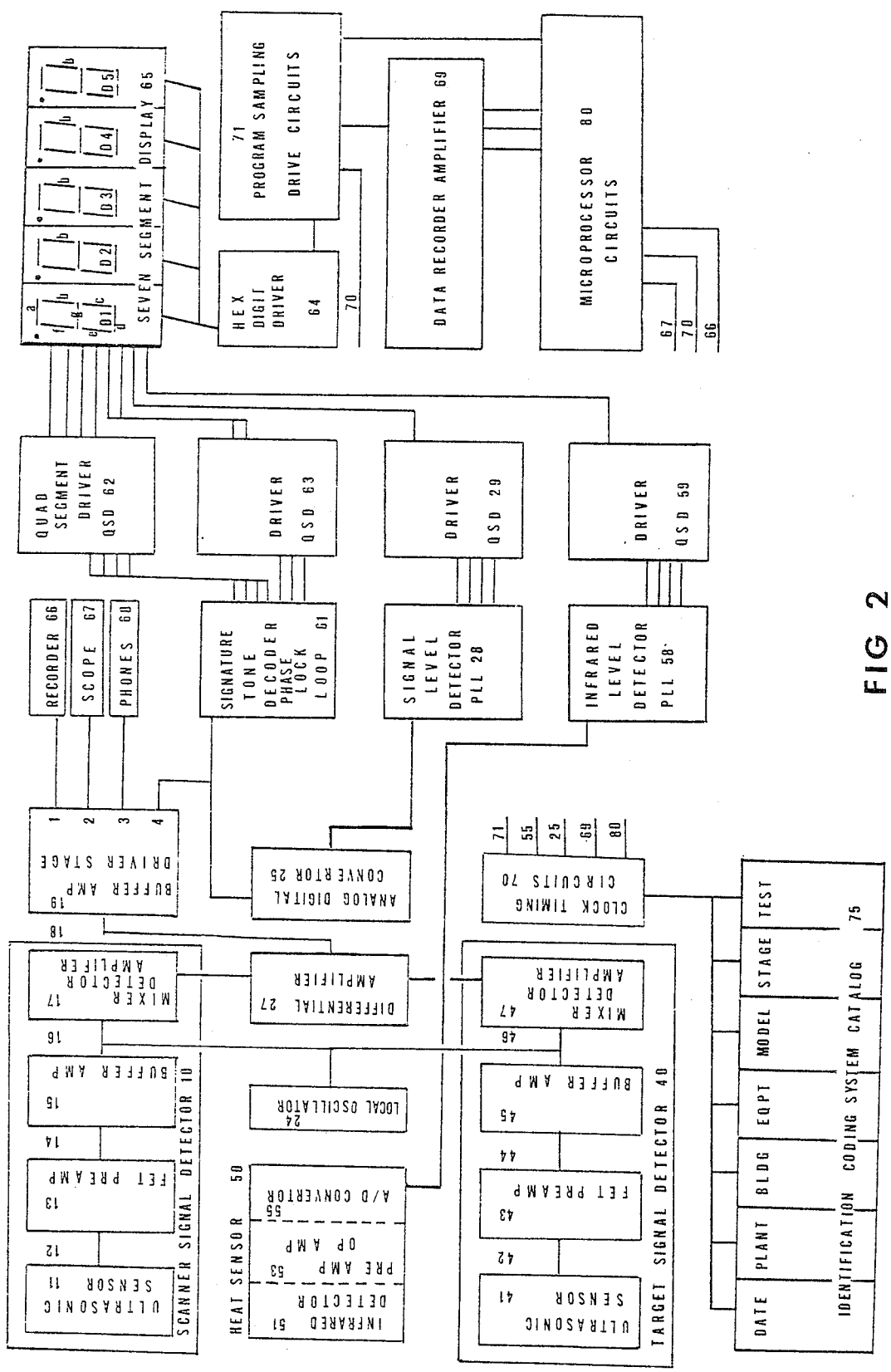
FIG. 2 is a schematic block diagram of the preferred apparatus.

Referring now to the schematic representation of FIG. 2, there is shown a scanner detector 10 having as its input an ultrasonic sensor 11, being selected for maximum response at the desired frequency "window", connected by a low loss cable 12 to an field effect transistor, FET preamplifier integrated circuit 13 and buffer stage 15 which is used to minimize undesirable feedback and loading effects. At the buffer amplifier stage output junction 16 the signal is joined with a stable signal from the local oscillator 24 tuned to a selected difference frequency above the frequency of the sensor 11. The selected composite difference frequency is combined in the mixer detector amplifier 17, amplified at this time due to the absence of signal at the negative input of the differential amplifier stage 27. Undesirable higher frequencies are shunted to ground and the difference frequency (audio) is further amplified and processed through the buffer amplifier amplifier 19 and driver stage 19-1,-2,-3,-4 to enable sufficient signal to drive the headphones 66, recorder 68, oscilloscope and additional circuitry discussed herein.

Scanning operational equipment will reveal signal perturbations present within the bandpass of sensor 11, which signal will be heard in headphones 66. This technique is most desirable in the expedient location of potential problem areas wherein the machinery can be scanned and an incipient malfunction can be bought to the attention of the maintenance engineer for service or adjustment to avoid failure or malfunction.

Closer observation of the problem area can be resolved by use of the target signal detector 40 which comprises circuitry similar to that of the scanner signal detector. Target sensor 41 is connected through a flexible cable 42 to the apparatus of this invention thereby enabling the target sensor 41 to be held closer to the suspect area. Provided the same signal from local oscillator 24, the target mixer detector amplifier 47 will deliver a signal to the negative input of differential amplifier 27 of the same approximate strength and phase relation as that of the Scanner Mixer Detector 17. These signals will therefore tend to cancel when the output of the target detector 40 and signal detector 10 are equal in phase, amplitude and frequency, each having substantially the same level of signal and the same level of noise from the same source. However, when the Scanner Detector is directed away from the equipment only the Target Detector will input the desired signal to be amplified, ambient noise signals being equal will cancel within circuits of the differential amplifier. Such action enables greater signal to noise ratio for better signal resolution and processing.

At some time it is necessary to compare history records of the same equipment component, and it becomes prudent to obtain specific component location for a given sample obtained from a potential problem area in such a manner that it can be identified as belonging to a particular test set. The Identification Coding System Catalog 75 will provide this information including date, customer, plant, frame, location and the like by coded identification compatible with the microprocessor.

In order to enable resolution of the wear history it is necessary to detect characteristic signal patterns or signatures modulated on the primary carrier frequency. An output from buffer amplifier 19 is parallel connected to a plurality of phase lock loop circuits 61 each tuned to a difference frequency to be detected from the carrier signal. When signals are present and of sufficient strength to overcome a predetermined level an output will be realized from the phase lock loop circuits 61. Many signals can be present at a given test sampling but only those selected frequencies to which the phase lock loop circuits are tuned will be available at the output of these circuits and cause the related quad-segment driver 62/63 to conduct. In this preferred embodiment Program drive circuits 71 allow the first of the seven segment displays 65 to activate during a period of turn-on time by sequencing the Hex-digit driver 64. Should sufficient signal strength be present at any phase lock loop circuit be present, the output of that circuit will function and the hex-digit driver 64 will sample the output of the quad-segment driver 62/63 allowing segments of the display to respond by illumination. Segments of successive displays respond to the same assigned frequencies, ie; $f_1 = D_{1a}, D_{2a}, \ldots$ successively a sampling will occur for each display when the test is initiated. When the identical signals are continuous each of the displays will indicate alike, ie; $65D_{1bce}, D_{2bce}, D_{3bce}, D_{4bce}, D_{5bce} \ldots$ when the program sampling circuits have completed the test cycle, this display indication is indicative of normal operational wear. Intermittent or spasmodic signals generally forecast abnormal operation. It should be noted that arbitrary signal frequency families have been selected and assigned each of the phase lock loop circuits for indicating carrier modulation and that such signals are selected with regard to the type equipment being monitored.

The assembly of this invention may further comprise an infrared detector circuit 50 to indicate the amount of heat present at a given location on the equipment being investigated. The infrared sensor detector 51 may be molded within the face of the apparatus, preferably adjacent to the target signal detector 41 and is amplified by the infrared pre-amp 53 and operational amplifier 54. Input to the analog digital converter 55 is a filtered RMS voltage output from the infrared detector circuits. This analog-to-digital converter signal is supplied to each input of the infrared phase lock loop detector circuits 58 in the same manner as previously explained for phase lock loop signal decoding. However, each output from the quad-segment driver 59 is connected to the lower segment (d) of the segmented display 65. The first of the phase lock loop circuits 58 which is tuned to the lowest output frequency of the A/D converter 55 is connected to segment 'd' of the first display and represents the lower heat level detected. Each successive phase lock loop 58 is tuned more broadly than the previous circuit to insure that tests indicating higher temperatures illuminate more than one segment of the displays. Surface temperatures greater than 100° C. will produce an audible alarm. In a like manner the RMS value of the signal level received at the A/D converter 25 will cause visual indications of increased signal levels by lighting the decimal character on the seven segment display.

When the test cycle is initiated by depressing the test sample switch grounding will cause a trigger from the timing circuits 70. Upon completion of the catalog coding sequence timing circuits 70 will trigger the program sampling circuits through four cycles per sample and five samples per test, one sample for each display. These circuits are then locked out and displays continue to indicate until program drive circuits remove the operating potential.

Finally, a data recording amplifier 69 serves as input to the recorder 68, during the test cycle only, which stores information for the microprocessor 80 and other evaluation processes and maintain a history file. Input from the buffer amplifier in drive stage 19 to recorder is not connected during the system test to avoid interaction with data files. Inputs to the data recorder amplifier 69 are hard wired to the identification coding system 75 and the quad segment drivers. Conduction of this recording amplifier is controlled by application of the operating potential to the circuits of this integrated circuit chip from the program drive circuits 71.

It will thus be seen that the objects set forth above, among those made apparent from the preceding description, are efficiently attained and, since certain changes may be made in the above construction without departing from the scope of the invention, it is intended that all matter contained in the above description or shown in the accompanying drawings shall be illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An apparatus for detecting an incipient failure of equipment which failure is characterized by the emission of ultrasonic signals from the equipment wherein the signals have a specific ultrasonic frequency distribution about a primary frequency, comprising, in combination:
   a first ultrasonic sensor for receiving the primary frequency signal generated by the equipment;
   a local oscillator for generating a signal selected to be a predetermined frequency difference relative to the primary frequency signal; and
   a second ultrasonic sensor for receiving ambient background noise operatively connected to said apparatus to substantially cancel ambient background noise, whereby said primary frequency will be better observed; and
   a mixer detector amplifier operatively connected to receive the outputs of said first and second ultrasonic sensors and of said local oscillator whereby the differences between said outputs may be detected to provide a demodulated frequency within a predetermined bandpass; and
   a means for processing said demodulated frequency.

2. An apparatus as in claim 1 further comprising an infrared sensor mounted substantially adjacent said first ultrasonic sensor for receiving heat emanating from the area generating said primary frequency, whereby an incipient failure of the equipment may be more accurately detected.

3. An apparatus as in claim 1 wherein said processing means comprises headphones.

4. An apparatus as in claim 1 wherein said processing means comprises an oscilloscope.

5. An apparatus as in claim 1 wherein said processing means comprises a recorder.

6. An apparatus as in claim 1 further comprising means for determining normal wear of equipment by analyzing signal patterns modulated on said primary frequency signal, said means comprising a plurality of selectively tuned phase lock loop circuits for determining a corresponding plurality of modulated signal patterns, said plurality of tuned phase lock loop circuits being operatively connected to receive said demodulated frequency; and a plurality of segmented displays each comprising plural segments, wherein each one of said segmented displays is operatively connected in receiving relation to the output of a corresponding one of said tuned phase lock loop circuits, whereby the results of sequential actuations of said apparatus will be sequentially displayed on individual segments of said plurality of segmented displays to permit the operator of said apparatus to observe visually the relative consistency of plural actuations of said apparatus.

7. An apparatus as in claim 6 further comprising means for determining the rate of change of said primary frequency signal, said means comprising a data recorder for storing data from primary frequency signal of a prior measurement; timer means; means for comparing successive frequency change of said primary frequency signal measurements as a function of time.

8. An apparatus as in claim 7 wherein said data recorder records test characteristics of said primary frequency signal measurements to enable comparison with earlier test history.

* * * * *